United States Patent
Algawi et al.

(10) Patent No.: US 10,537,350 B2
(45) Date of Patent: Jan. 21, 2020

(54) MEDICAL DEVICE HAVING A REUSABLE POSITION SENSOR

(71) Applicant: Biosense Webster (Israel) Ltd., Yokneam (IL)

(72) Inventors: Yehuda Algawi, Binyamina (IL); Assaf Govari, Haifa (IL); Ilya Sitnitsky, Nahariya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 247 days.

(21) Appl. No.: 15/471,766

(22) Filed: Mar. 28, 2017

(65) Prior Publication Data
US 2018/0280049 A1    Oct. 4, 2018

(51) Int. Cl.
| | |
|---|---|
| *A61B 17/32* | (2006.01) |
| *A61B 17/24* | (2006.01) |
| *A61B 90/98* | (2016.01) |
| *A61B 34/20* | (2016.01) |
| *A61B 17/00* | (2006.01) |
| *A61B 90/00* | (2016.01) |

(52) U.S. Cl.
CPC .............. *A61B 17/32* (2013.01); *A61B 17/24* (2013.01); *A61B 17/32002* (2013.01); *A61B 34/20* (2016.02); *A61B 90/98* (2016.02); *A61B 2017/0023* (2013.01); *A61B 2017/0046* (2013.01); *A61B 2017/320004* (2013.01); *A61B 2034/2051* (2016.02); *A61B 2090/0811* (2016.02)

(58) Field of Classification Search
CPC ... A61B 17/24; A61B 17/32; A61B 17/32002; A61B 34/20; A61B 2017/0023; A61B 2017/0046; A61B 2017/320004; A61B 2034/2051; A61B 2090/0811
See application file for complete search history.

(56) References Cited

U.S. PATENT DOCUMENTS

| | | |
|---|---|---|
| 5,391,199 A | 2/1995 | Ben-Haim |
| 5,803,089 A | 9/1998 | Ferre et al. |
| 6,239,724 B1 | 5/2001 | Doron et al. |

(Continued)

FOREIGN PATENT DOCUMENTS

| | | |
|---|---|---|
| WO | WO 96/05768 A1 | 2/1996 |
| WO | WO 2003/013372 A2 | 2/2003 |
| WO | WO 2007/084893 A2 | 7/2007 |

OTHER PUBLICATIONS

European Search Report dated Aug. 7, 2018 for Application No. 18164222.4, 6 pages.
(Continued)

*Primary Examiner* — Jocelin C Tanner
(74) *Attorney, Agent, or Firm* — Frost Brown Todd LLC

(57) ABSTRACT

A medical device includes a disposable Ear-Nose-Throat (ENT) tool, a reusable handle, and a processor. The ENT tool is configured to perform a medical procedure in a patient ENT organ. The reusable handle is configured to hold and control the disposable ENT tool, and includes a position sensor configured to produce one or more position signals that are indicative of a first position of the reusable handle. The processor is configured to receive the position signals from the position sensor, and to estimate, based on the position signals, a second position of the disposable ENT tool in the patient ENT organ.

17 Claims, 2 Drawing Sheets

(56) References Cited

U.S. PATENT DOCUMENTS

| | | |
|---|---|---|
| 6,332,089 B1 | 12/2001 | Acker et al. |
| 6,332,891 B1 * | 12/2001 | Himes ................ A61B 90/36 |
| | | 606/130 |
| 6,434,507 B1 | 8/2002 | Clayton et al. |
| 6,484,118 B1 | 11/2002 | Govari |
| 6,618,612 B1 | 9/2003 | Acker et al. |
| 6,690,963 B2 | 2/2004 | Ben-Haim et al. |
| 8,504,139 B2 | 8/2013 | Jacobsen et al. |
| 8,858,495 B2 | 10/2014 | Tegg et al. |
| 9,427,279 B2 | 8/2016 | Muniz-Medina et al. |
| 2002/0065455 A1 | 5/2002 | Ben-Haim |
| 2003/0120150 A1 | 6/2003 | Govari |
| 2003/0208122 A1 * | 11/2003 | Melkent ................ A61B 5/06 |
| | | 600/426 |
| 2004/0068178 A1 | 4/2004 | Govari |
| 2006/0004286 A1 * | 1/2006 | Chang ................ A61B 5/06 |
| | | 600/435 |
| 2008/0188848 A1 | 8/2008 | Deutmeyer et al. |
| 2008/0200926 A1 | 8/2008 | Verard et al. |
| 2008/0211634 A1 | 9/2008 | Hopkins et al. |
| 2009/0234232 A1 * | 9/2009 | Gertsen ................ A61B 8/4461 |
| | | 600/459 |
| 2011/0015667 A1 * | 1/2011 | Gonzales ................ A61B 17/24 |
| | | 606/196 |
| 2011/0022172 A1 | 1/2011 | Gonzales et al. |
| 2011/0303836 A1 * | 12/2011 | Gibson ................ G01T 3/00 |
| | | 250/267 |
| 2012/0078377 A1 | 3/2012 | Gonzales et al. |
| 2015/0223831 A1 | 8/2015 | Bickenbach |

OTHER PUBLICATIONS

European Communication dated Jul. 11, 2019 for Application No. 18164222.4, 5 pages.

* cited by examiner

MEDICAL DEVICE HAVING A REUSABLE POSITION SENSOR

FIELD OF THE INVENTION

The present invention relates generally to medical devices, and particularly to methods and systems for tracking a position of an Ear-Nose-Throat (ENT) tool in a patient body.

BACKGROUND OF THE INVENTION

Position sensors of a position tracking system may be mounted on various medical devices for tracking the position of the medical device in a patient body.

For example, U.S. Pat. No. 5,803,089, whose disclosure is incorporated herein by reference, describes a system for monitoring the position of a medical instrument with respect to a patient's body and for displaying at least one of a plurality of prerecorded images of said body responsive to the position of said medical instrument. A field generator may be associated with one of the units for generating a position characteristic field in an area including the target operation site. One or more field sensors may be associated with either of the units responsive to the presence of the position characteristic field for producing one or more sensor output signals representative of said sensed field.

U.S. Pat. No. 6,434,507, whose disclosure is incorporated herein by reference, describes an apparatus that comprises a tool body and tool attachment onto which emitters are fixedly mounted. At least one tool tip is coupled with the tool body in a removable manner. An electrical sensor is positioned to be operated when the tool tip is changed either by coupling the tip to or removing the tip from the tool body.

SUMMARY OF THE INVENTION

An embodiment of the present invention that is described herein provides a medical device including a disposable Ear-Nose-Throat (ENT) tool, a reusable handle, and a processor. The ENT tool is configured to perform a medical procedure in a patient ENT organ. The reusable handle is configured to hold and control the disposable ENT tool, and includes a position sensor configured to produce one or more position signals that are indicative of a first position of the reusable handle. The processor is configured to receive the position signals from the position sensor, and to estimate, based on the position signals, a second position of the disposable ENT tool in the patient ENT organ.

In some embodiments, the reusable handle is configured to control positioning of the ENT tool in a predefined debriding site in the patient ENT organ, and the disposable ENT tool is configured to debride tissue when positioned at the debriding site. In other embodiments, the disposable ENT tool is configured to acquire one or more anatomical images in the patient ENT organ. In yet other embodiments, the medical device includes a remotely readable memory, which is coupled to the disposable ENT tool and is configured to store a value indicative of an offset vector between the first position and the second position.

In an embodiment, the processor is configured to read the value stored in the remotely readable memory and to estimate the second position based on the value and the first position. In another embodiment, the remotely readable memory includes a Radio-Frequency Identification (RFID) tag.

In some embodiments, the medical device includes a housing, which contains the reusable handle and is configured to block external radiation from distorting the position signals. In other embodiments, the housing includes titanium.

There is additionally provided, in accordance with an embodiment of the present invention, a method including, inserting into a patient body a disposable Ear-Nose-Throat (ENT) tool that applies a medical procedure in a patient ENT organ. One or more position signals that are indicative of a first position of a reusable handle, are received from a position sensor, which is coupled to the reusable handle that is external to the patient ENT organ and holds and controls the ENT tool. Based on the first position signals, a second position of the disposable ENT tool in the patient ENT organ is estimated. The disposable ENT tool is navigated to a target location in the patient ENT organ by setting the second position at the target location. The medical procedure is applied at the target location.

The present invention will be more fully understood from the following detailed description of the embodiments thereof, taken together with the drawings in which:

DETAILED DESCRIPTION OF EMBODIMENTS

Overview

Figure 1:
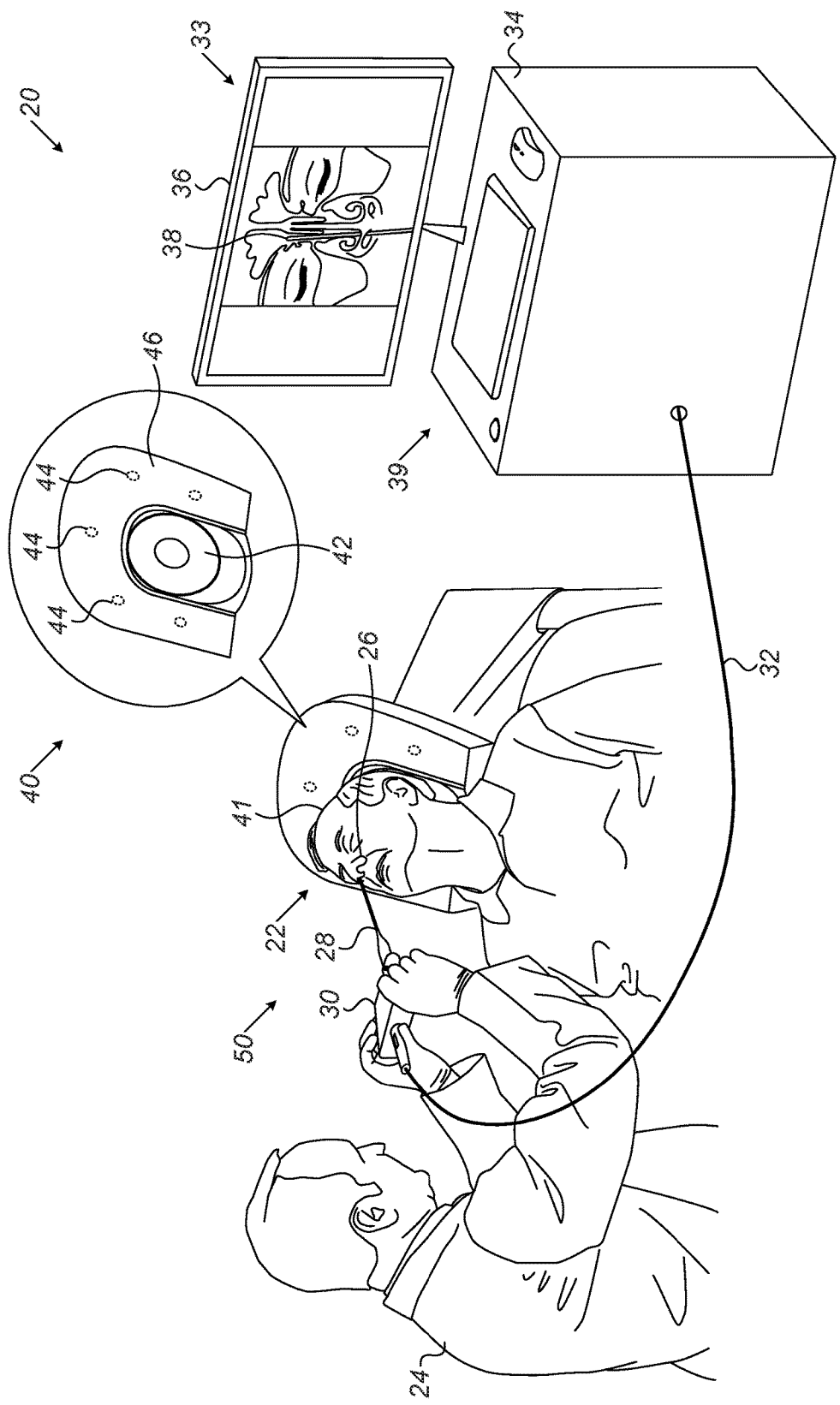
FIG. 1 is a schematic, pictorial illustration of a sinuplasty procedure using an Ear-Nose-Throat (ENT) treatment system, in accordance with an embodiment of the present invention.

Position tracking systems may be used in various medical applications for assisting the navigation of a medical device in a patient body. For example, such a tracking system can be used in sinuplasty, for navigating a suitable surgical device in an Ear-Nose-Throat (ENT) organ of the patient.

Embodiments of the present invention that are described hereinbelow provide improved techniques for reducing the cost and complexity of disposable medical devices that require position tracking, and for shortening the cycle time of medical procedures that use such devices. These techniques can be used, for example, in a sinuplasty procedure, in which the physician needs to track the position of a rigid tool within the ENT organ of a patient.

In some embodiments, an ENT device comprises a disposable diagnostics and/or surgical tool (also referred to as an ENT tool), and a reusable handle that is held by a physician and configured to hold and control the ENT tool. In principle, for tracking the position of the ENT tool within the ENT organ, it is possible to fit a position sensor at the distal tip of the disposable tool, and to calibrate the position sensor relative to the coordinate system of the position tracking system. Since, however, the ENT tool is disposable, the sensor will be disposed of together with the ENT tool after performing a sinuplasty procedure, and another sensor will have to be calibrated relative to the coordinate system of the position tracking system before performing a subsequent sinuplasty procedure.

In some embodiments, a position sensor is coupled to the reusable handle of the ENT device (instead of to the disposable ENT tool), and therefore the same sensor can be reused in subsequent sinuplasty procedures. Note that by using this approach, the sensor measures the position of the handle and not the position of the tip of the ENT tool, and therefore the measurement should be corrected accordingly. In some embodiments, a processor of the position tracking system is configured to store and apply an offset vector that specifies the difference in position between the position sensor and the distal tip of the ENT tool.

In some cases, the offset vector may differ from one ENT tool to another, for example due to differences in length and shape among ENT tools of the same type (e.g., due to variations in production), or in case the same handle is used to control different types of ENT tools. In some embodiments, a remotely readable memory device, such as a Radio-Frequency Identification (RFID) tag, may be mounted on the tool. The RFID tag is configured to store the value of the offset vector specific to the ENT tool on which it is mounted. In an embodiment, the processor of the position tracking system is configured to read the offset vector from the RFID tag, and to estimate the actual position of the distal tip of the ENT tool in the ENT organ based on the position signal provided by the sensor and the offset vector.

In some embodiments, the handle comprises a housing made from titanium, which is a light-weight biocompatible material that also blocks external radiation from distorting the position signals measured by the position sensor.

The disclosed techniques reduce the physical weight and cost of the ENT device by using light-weight materials and by reusing the position sensor in multiple sinuplasty procedures. Furthermore, a single handle can hold and control different types of ENT tools by storing the offset vector of each ENT tool on its RFID tag. The disclosed techniques are particularly applicable in sinuplasty procedures in which rigid ENT tools are commonly used.

SYSTEM DESCRIPTION

FIG. 1 is a schematic pictorial illustration of a sinuplasty procedure using an Ear-Nose-Throat (ENT) treatment system 20, in accordance with an embodiment of the present invention. System 20 comprises an ear-nose-throat (ENT) treatment device 50 that comprises a disposable ENT tool 28, used for diagnostics and/or surgical applications, which is fitted at a distal end of device 50. During the sinuplasty procedure, a physician 24 inserts tool 28 into a nose 26 of a patient 22 so as to treat or diagnose an ENT disease. For example, the treatment may involve shaving tissue in one or more sinuses of patient 22. The terms "shaving" and "debriding," as well as "shaver" and "debrider," are used in the present disclosure interchangeably, and refer to the process or the tools used for cutting tissue from an organ of patient 22.

In some embodiments, tool 28 may comprise a shaver (not shown), which is configured to shave the tissue, and one or more pipes (shown in FIG. 2), which are configured to draw the shaved tissue from at least one of the sinuses. In other embodiments, tool 28 may further comprise any suitable device such as an imaging device, which is configured to acquire images of an ENT organ of patient 28. Device 50 further comprises a handle 30, which is coupled to the proximal end of ENT tool 28, and configured to hold and control a distal tip 38 of tool 28. Device 50 is depicted in detail in FIG. 2 below.

In an embodiment, system 20 further comprises a magnetic position tracking system, which is configured to track the position of one or more position sensors in the head of patient 22 or in close proximity to the ENT organ of patient 22. The magnetic position tracking system comprises magnetic field-generators 44 and one or more position sensors (shown in FIG. 2). The position sensors generate position signals in response to the sensed external magnetic fields generated by field generators 44, thereby enabling a processor 34 to map the position of each sensor as will be described below.

This method of position sensing is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004, 2003/0120150 A1, issued as U.S. Pat. No. 7,729,742 on Jun. 1, 2010 and 2004/0068178 A1, now abandoned, whose disclosures are all incorporated herein by reference.

System 20 further comprises a location pad 40, which comprises field-generators 44 fixed on a frame 46. In the exemplary configuration shown in FIG. 1, pad 40 comprises five field-generators 44, but may comprise any other suitable number of generators 44. Pad 40 further comprises a pillow 42 placed under a head 41 of patient 22, such that generators 44 are located at fixed, known positions external to the patient.

In some embodiments, handle 30 comprises a magnetic position sensor (shown in FIG. 2 below). System 20 further comprises a console 33, which comprises processor 34, typically a general-purpose computer, with suitable front end and interface circuits for receiving signals from the magnetic position sensor, via a cable 32, and for controlling other components of system 20 described herein.

In an embodiment, console 33 comprises a driver circuit (not shown), which is configured to drive field-generators 44 with suitable signals so as to generate magnetic fields in a predefined working volume around head 41.

FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description.

Processor 34 may be programmed in software to carry out the functions that are used by the system, and to store data in a memory (not shown) to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Figure 2:
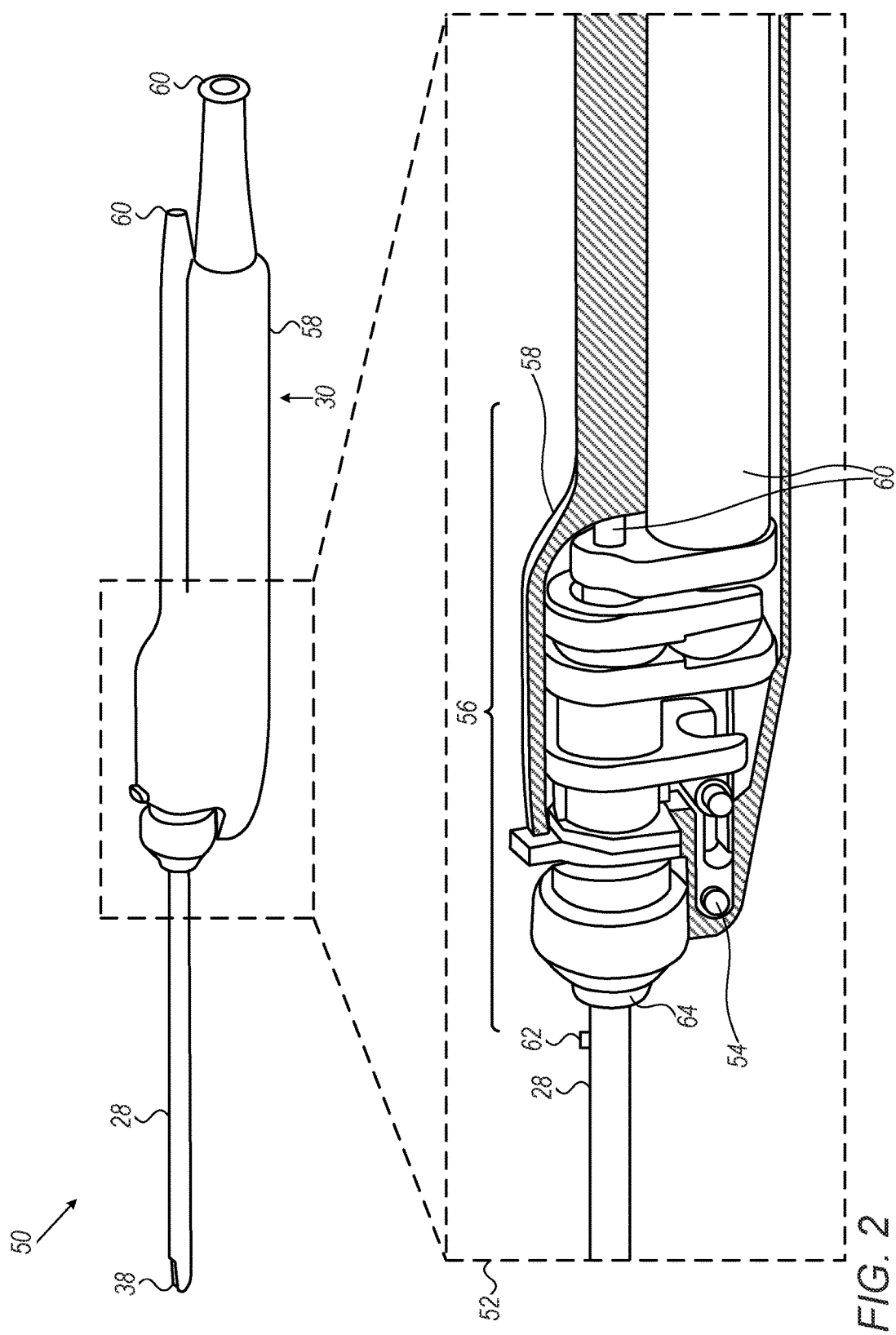
FIG. 2 is a schematic, pictorial illustration of an ENT device of the ENT treatment system, in accordance with an embodiment of the present invention.

FIG. 2 is a schematic, pictorial illustration of ENT device 50, in accordance with an embodiment of the present invention. In some embodiments, ENT tool 28 is made from a rigid biocompatible material such as stainless-steel SS316 and SS316L, and titanium. In some embodiments, ENT tool 28 comprises a sinuplasty diagnostics and/or surgical tool, such as a shaver, located at distal tip 38. During the sinuplasty procedure, physician 24 typically inserts ENT tool 28 into nose 26 so that ENT tool 28 is in direct contact with ENT organs (and possibly blood) of patient 22, thus, tool 28 is typically disposed of after the sinuplasty procedure.

In some embodiments, handle 30 comprises one or more pipes 60, which may be used for irrigating antiseptic and/or cooling fluids, and for drawing the shaved tissue out of the ENT organ of patient 22.

Reducing the Sinuplasty Costs by Minimizing the Number of Disposable Elements In some embodiments, handle 30 remains out of the body of patient 22 during the sinuplasty procedure, and therefore, it is reusable for use in multiple procedures. In order to reduce the overall cost of a sinuplasty procedure, it is important to minimize the number and cost of elements within tool 28, which are disposable.

Reference is now made to an inset 52 at the bottom of FIG. 2. In some embodiments, handle 30 comprises a mechanical assembly 56, which is configured to drive (e.g., rotate) the sinuplasty shaver, so as to shave the tissue, and/or to transfer fluids, via pipes 60, to/from the treated sinus.

In principle, it is possible to fit a position sensor (not shown) at distal tip 38, so as to measure the position of the shaver in the ENT organ. In this configuration, however, the position sensor will be disposed of, as it is contained within tool 28 that is typically disposable as a complete unit. Furthermore, this configuration requires integrating electrical leads within tool 28, so as to transmit the position signals between the position sensor and processor 34. The leads have to fit in a tight space within tool 28, are not allowed to rotate with the shaver, require a connector in the interface between tool 28 and handle 30, and are eventually disposed of with tool 28.

In some embodiments, the shortcomings of coupling a position sensor to tool 28 are overcome by instead coupling a position sensor 54 to handle 30. Sensor 54 may be coupled to the handle at any suitable location, so as to produce one or more position signals that are indicative of the position of handle 30 in a coordinate system of the position tracking system.

In an embodiment, processor 34 is configured to store a value of an offset vector of the handle, referred to herein as "H-vector", which is a constant offset between the coordinates of a mechanical connector 64 (that connects tool 28 to handle 30) and the coordinates of position sensor 54.

In principle, each tool 28 has its own length and shape. A value of an offset vector between the coordinates of the proximal end of tool 28 (the point of connection to connector 64) and the coordinates of distal tip 38 of ENT tool 28 is referred to as a tool vector, or "T-vector". Note that ENT tool 28 is typically rigid, therefore, the T-vector of each tool 28 is constant.

In some cases, the T-vector may differ from one ENT tool to another, for example in case physician 22 uses the same handle to control different types of ENT tools (having different values of T-vectors) during the ENT procedure. Furthermore, process variations in the production of the ENT tools may cause differences in length and shape among ENT tools of the same type.

In some embodiments, tool 28 may comprise a remotely readable memory, such as a Radio-Frequency Identification (RFID) tag 62, which is configured to store the T-vector. In some embodiments, for each individual tool 28, the specific T-vector measured for that tool is stored in the tool's RFID tag 62. In these embodiments, tools 28 of the same type may have different T-vectors. In other embodiments, the T-vectors of all tools 28 of the same type are set to the same value. Storage of the T-vectors in tags 62 is typically performed during production of tools 28, but may alternatively be carried out at any other suitable time.

In the example of FIG. 2, the T-vector between connector 64 and distal tip 38 may be represented by a magnitude (e.g., in millimeters) and direction (e.g., in degrees of rotation and inclination relative to the longitudinal axis of handle 30). Alternatively, the T-vector may be represented by three Cartesian coordinates in a predefined coordinate system of handle 30, or using any other suitable representation.

In some embodiments, processor 34 is configured to read the T-vector stored in RFID tag 62, and to sum the H-vector and the T-vector. The vector sum represents the magnitude and direction between position sensor 54 and distal tip 38, and is referred to as "ST-vector" (sensor-to-tip vector).

In an embodiment, processor 34 is configured to sum the coordinates of the ST-vector and the respective coordinates measured by position sensor 54, so as to estimate the respective position of distal tip 38 in the coordinate system of the position tracking system.

In practice, after being coupled to handle 30, position sensor 54 has to be calibrated relative to the coordinate system of the position tracking system. In some embodiments, coupling sensor 54 to handle 30 allows reusing sensor 54 in multiple sinuplasty procedures, thereby saving the cost of the sensor hardware, and eliminating the need to recalibrate sensor 54 (relative to the position tracking system) before the subsequent sinuplasty procedure.

Note that the value of the T-vector depends on the geometry of the rigid ENT tool (and not on the geometry of the handle), and that the value of the H-vector depends on the geometry of the handle (and not of the ENT tool). As a result, physician 24 has the flexibility to use ENT tools of different shapes (and respective T-vectors) with handles of various shapes (and respective H-vectors) without any adjustments of the T-vector or H-vector.

Typically, physician 24 holds handle 30 during the sinuplasty procedure. Therefore, it is important to reduce the overall weight of device 50, and in particular, of handle 30. In some embodiments, handle 30 comprises a housing 58, which contains mechanical assembly 56 and other components of the reusable handle. In an embodiment, housing 58 is made from a light biocompatible material, such as titanium, which reduces the overall weight of handle 30.

In some cases, external radiation may induce eddy currents that may flow on the surface of handle 30. The eddy currents may interfere, for example, with the position signals of position sensor 54, thereby reducing the accuracy of the position tracking system. In some embodiments, housing 58, which is made from a suitable material having low electrical conductivity, such as titanium, is configured to prevent (or at least weaken) the interfering eddy currents.

The configuration of device 50 is an exemplary configuration, which is chosen purely for the sake of conceptual clarity. In alternative embodiments, the disclosed techniques can be used, mutatis mutandis, in various other configurations of system 20 and device 50.

For example, RFID tag 62 may be coupled to ENT tool 28 at any suitable location. Alternatively or additionally, in case physician 24 uses the same type of tool 28, high uniformity in the production of tools 28 may eliminate the need for RFID tag 62 by storing (e.g., in processor 34) a constant offset between position sensor 54 and distal tip 38.

Although the embodiments described herein mainly address ENT procedures, the methods and systems described herein can also be used in other applications, such as in any diagnostic or surgical application.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical device, comprising:
   (a) a disposable Ear-Nose-Throat tool, which is configured to perform a medical procedure in a patient Ear-Nose-Throat location, wherein the disposable Ear-Nose-Throat tool comprises:
      (i) a distal tip,
      (ii) a proximal end, and
      (ii) a remotely readable memory comprising a first offset vector indicative of a displacement between the distal tip and the proximal end;
   (b) a reusable handle, which is configured to hold and control the disposable Ear-Nose-Throat tool at the proximal end via a mechanical connector, wherein the reusable handle comprises a position sensor configured to produce one or more position signals that are indicative of a first position of the sensor; and
   (c) a processor storing a second offset vector indicative of a displacement between the mechanical connector and the sensor, wherein the processor is configured to read the remotely readable memory of the disposable Ear-Nose-Throat tool to obtain the first offset vector, wherein the processor is configured to receive the position signals from the position sensor, and to estimate, based on a combination of the first offset vector, the second offset vector, and the one or more position signals, a position of the distal tip in the patient Ear-Nose-Throat location.

2. The medical device according to claim 1, wherein the reusable handle is configured to control positioning of the Ear-Nose-Throat tool in a predefined debriding site in the patient Ear-Nose-Throat location, and wherein the disposable Ear-Nose-Throat tool is configured to debride tissue when positioned at the debriding site.

3. The medical device according to claim 1, wherein the distal tip of the disposable Ear-Nose-Throat tool comprises an imaging device that is configured to acquire one or more anatomical images in the patient Ear-Nose-Throat location.

4. The medical device according to claim 1, wherein the remotely readable memory comprises a Radio-Frequency Identification tag.

5. The medical device according to claim 1, and comprising a housing, which contains the reusable handle and is configured to block external radiation from distorting the position signals.

6. The medical device according to claim 5, wherein the housing comprises titanium.

7. The medical device of claim 1, wherein the reusable handle further comprises a housing containing the position sensor.

8. The medical device of claim 7, wherein the reusable handle further comprising a first pipe.

9. The medical device of claim 8, wherein the reusable handle further comprises a second pipe.

10. The medical device of claim 1, wherein the position sensor is configured to produce the one or more position signals in response to a magnetic field.

11. The medical device of claim 1, wherein the position sensor further comprises a magnetic position sensor.

12. The medical device of claim 1, further comprising a console, wherein the console is in electrical communication with the processor.

13. The medical device of claim 12, wherein the console is configured to drive a plurality of field-generators.

14. A method, comprising:
   (a) receiving a data from a remotely readable memory attached to a disposable Ear-Nose-Throat tool that applies a medical procedure in a patient Ear-Nose-Throat location, wherein the data comprises a first offset vector indicative of a displacement between a distal tip and a proximal end of the disposable Ear-Nose-Throat tool,
   (d) receiving from a position sensor, which is coupled to a reusable handle that is external to the patient Ear-Nose-Throat location and holds and controls the Ear-Nose-Throat tool, one or more position signals that are indicative of a first position of the reusable handle;
   (c) estimating, based on a first position signal, the first offset vector, and a second offset vector indicative of a displacement between the position sensor and a mechanical coupling between the disposable Ear-Nose-Throat tool and the reusable handle, a position of distal tip of the disposable Ear-Nose-Throat tool in the patient Ear-Nose-Throat location;
   (d) navigating the disposable Ear-Nose-Throat tool to a target location in the patient Ear-Nose-Throat location by setting a second position at the target location.

15. The method according to claim 14, further comprising applying the medical procedure at the target location, wherein the target location comprises a debriding site, and wherein applying the medical procedure comprises debriding tissue when the disposable Ear-Nose-Throat tool is positioned at the debriding site.

16. The method according to claim 14, further comprising applying the medical procedure, wherein applying the medical procedure comprises acquiring one or more anatomical images in the target location.

17. A medical device, comprising:
   (a) a disposable Ear-Nose-Throat tool, which is configured to perform a medical procedure in a patient, wherein the disposable Ear-Nose-Throat tool comprises:
      (i) a distal tip,
      (ii) a readable memory, wherein the readable memory comprises a data comprising a first offset vector indicative of a position of the distal tip, and
   (b) a reusable handle, which is configured to hold and control the disposable Ear-Nose-Throat tool, wherein the reusable handle comprises a position sensor configured to produce one or more position signals that are indicative of a first position of the sensor; and
   (c) a processor storing a second offset vector indicative of a position of the sensor relative to a mechanical coupling between the reusable handle and the disposable Ear-Nose-Throat tool, wherein the processor is configured to receive the position signals from the position sensor, and to estimate a position of the distal tip in the patient, based on the position signals, the first offset vector, and the second offset vector.

* * * * *